United States Patent
Hintz

(10) Patent No.: US 9,301,820 B2
(45) Date of Patent: Apr. 5, 2016

(54) FLOSS DISPENSING TOOTHPASTE CAP

(71) Applicant: John Karl Hintz, Hayden, ID (US)

(72) Inventor: John Karl Hintz, Hayden, ID (US)

( * ) Notice: Subject to any disclaimer, the term of this patent is extended or adjusted under 35 U.S.C. 154(b) by 0 days.

(21) Appl. No.: 14/483,017

(22) Filed: Sep. 10, 2014

(65) Prior Publication Data
US 2016/0067020 A1 Mar. 10, 2016

(51) Int. Cl.
*A61C 15/00* (2006.01)
*A61C 15/04* (2006.01)

(52) U.S. Cl.
CPC ............. *A61C 15/043* (2013.01); *A61C 15/046* (2013.01)

(58) Field of Classification Search
CPC .................. A46B 15/0071; A46B 2200/1066; A46B 15/0055; A61C 15/046; A61C 15/043; A61C 15/048; A61C 15/02; A61C 15/041
USPC ........................... 132/309, 323, 324, 325, 329
See application file for complete search history.

(56) References Cited

U.S. PATENT DOCUMENTS

| | | | |
|---|---|---|---|
| 1,439,076 A | 12/1922 | Edwards | |
| 1,492,836 A | 5/1924 | Decker | |
| 1,733,114 A | 10/1929 | Brennan | |
| 1,858,134 A | 5/1932 | Booth et al. | |
| 4,428,389 A * | 1/1984 | Sanchez Cordero . | A61C 15/043 132/325 |
| 4,796,783 A * | 1/1989 | Paulson ............... | A61C 15/043 132/286 |
| 5,076,302 A | 12/1991 | Chari | |
| 5,732,722 A | 3/1998 | Mortvedt | |
| 5,979,706 A | 11/1999 | Grussmark | |
| 6,557,728 B1 | 5/2003 | Anderson et al. | |
| D493,014 S | 7/2004 | Hadtke et al. | |
| 7,243,663 B1 | 7/2007 | Einstein et al. | |
| 8,006,709 B1 * | 8/2011 | Ebnayamin ................... | 132/325 |
| 8,381,743 B1 | 2/2013 | Thomas et al. | |

FOREIGN PATENT DOCUMENTS

| | | | |
|---|---|---|---|
| CN | 101486395 A * | 7/2009 | |
| DE | 19730309 A1 * | 6/1998 | |
| GB | 2333276 A * | 7/1999 | ........... A61C 15/043 |
| KR | 20110000943 U * | 1/2011 | |
| WO | WO 0113816 A1 * | 3/2001 | |
| WO | WO 2004110295 A2 * | 12/2004 | |

* cited by examiner

*Primary Examiner* — Robyn Doan
(74) *Attorney, Agent, or Firm* — Wells St. John P.S.

(57) ABSTRACT

A floss dispensing toothpaste cap having a top portion connected to a bottom portion by a hinge region. An enclosure cavity encloses a removable floss spool. A floss cutter and a floss dispenser opening pass through a side of the bottom portion. A region of the top portion reversibly covers the floss dispensing opening and floss cutter. A floss-dispensing toothpaste cap includes a bottom portion having an enclosure with a connector to connect the cap onto a toothpaste tube. A nozzle is on the bottom portion opposing the connector. A floss cutter is on a side of the bottom portion. A removable floss spool is seated over the connector within the enclosure. A top portion is connected to the bottom portion by a hinge region, and has a tab that extends over a side of the bottom cap portion covering the floss cutter in a closed position.

8 Claims, 5 Drawing Sheets

FLOSS DISPENSING TOOTHPASTE CAP

TECHNICAL FIELD

The invention is related to hygienic dental floss dispensers that are combined with a toothpaste-dispensing cap for a container of toothpaste.

BACKGROUND OF THE INVENTION

Conventionally, dental floss is provided in a single purpose floss dispenser that is separate from any toothpaste source. Alternatively, floss dispensers have been externally connected to a toothpaste cap or floss is dispensed from caps having a floss cutter located in a non-covered area of the cap. Such configurations can be inconvenient and/or non-hygienic. It would be beneficial to develop alternative devices for dispensing dental floss.

SUMMARY OF THE INVENTION

The invention encompasses floss dispensing cap devises having a floss dispenser in combination with a toothpaste cap. A bottom portion of the cap connects to the nozzle of a toothpaste tube, includes a nozzle for dispensing toothpaste and includes an enclosure cavity for retaining a spool of dental floss. A floss dispenser opening and a floss cutter are disposed through a sidewall of the bottom portion. A top portion of the cap is connected to the bottom portion by a hinge region and closes over the bottom portion with a tab of the top portion covering the floss dispensing opening and the floss cutter.

The invention further encompasses toothpaste caps having internal spool of floss and a tab portion that reversibly covers floss leader, a floss dispensing opening through the cap and a floss cutter.

BRIEF DESCRIPTION OF THE DRAWINGS

Preferred embodiments of the invention are described below with reference to the following accompanying drawings.

DETAILED DESCRIPTION OF THE PREFERRED EMBODIMENTS

This disclosure of the invention is submitted in furtherance of the constitutional purposes of the U.S. Patent Laws "to promote the progress of science and useful arts" (Article 1, Section 8).

The invention pertains to toothpaste cap devices with integrated floss dispensers. The invention is described generally with reference to FIGS. 1-6.

Figure 1:
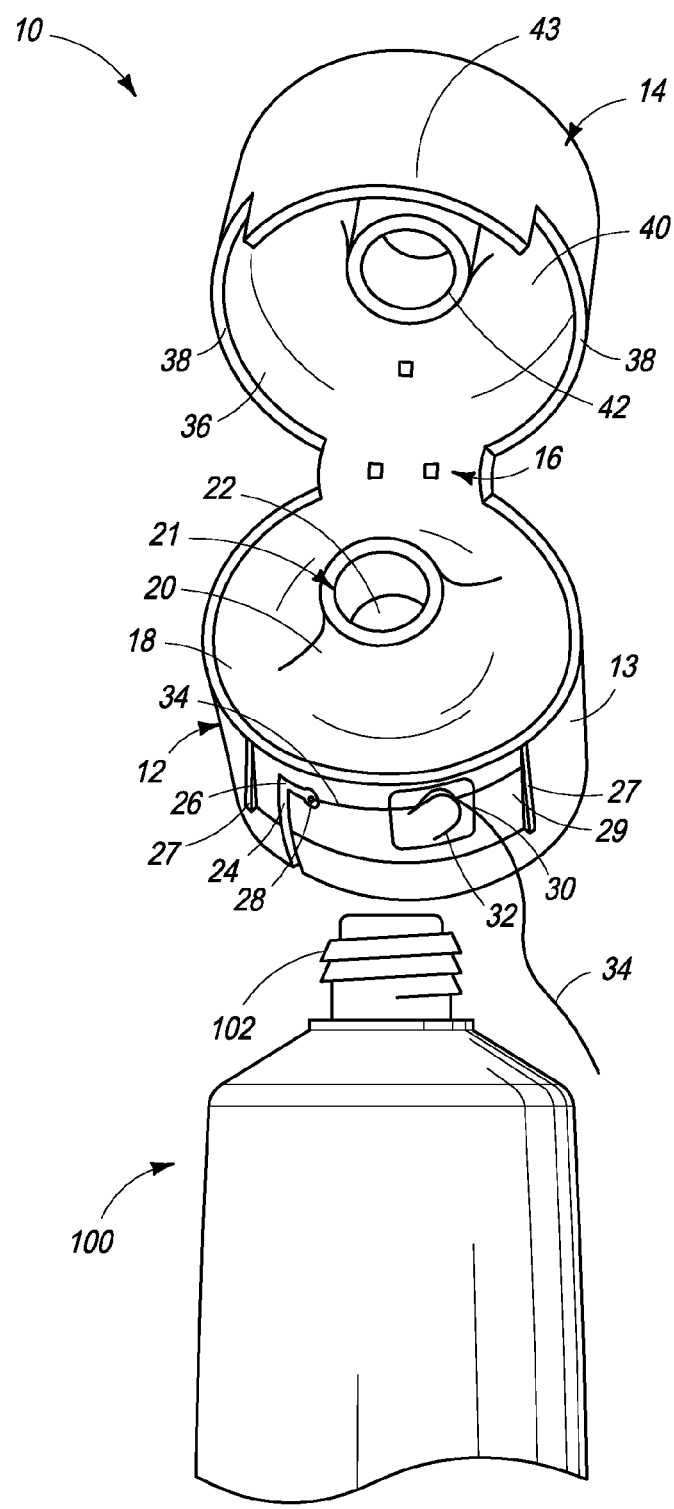
FIG. 1 illustrates a side view of one embodiment of the invention.

Referring initially to FIG. 1, such depicts a particular embodiment of the invention comprising floss-dispensing cap device 10 illustrated in an "open" position. Device 10 can include a bottom cap portion 12 and an upper cap portion 14 configured to close onto the bottom cap portion 12 (see FIG. 3). Bottom cap portion 12 can be joined to upper cap portion 14 by a hinge region 16 that is attached to both the lower cap portion and the upper cap portion as depicted in FIG. 1. The two portions 12, 14 of device 10 can be moved from an open position (FIG. 1) to a closed position (FIG. 3) by manipulation (opening and closing) of hinge region 16.

Device 10 can comprise a single-piece structure that includes the bottom cap portion, the upper cap portion and the hinge region. The single piece configuration can be formed by, for example, injection molding utilizing, for instance, any moldable type plastic that remains flexible upon curing.

Device 10 can be configured to seat onto a toothpaste container 100 and can be cylindrical in certain embodiments. The outer diameter of device 10 can be, for example, approximately 3.5 cm-4.0 cm, however other sizes are contemplated. It is to be understood that although the invention is described and illustrated with respect to a tube type of toothpaste container, the invention contemplates alternative configurations of the cap device that can be utilized in conjunction with alternative container types. Accordingly, alternative shapes of device 10 are contemplated. Additionally, the overall height of device 10 and its upper and bottom portions are not limited to any particular values. An example overall height of device 10 can be about 2.75 cm or greater, with an example upper portion height of 1.5 cm and an example bottom portion height of 1.25 cm.

In particular aspects, bottom portion 12 of device 10 can thread onto a threaded nozzle 102 of toothpaste container 100 (discussed below). Bottom cap portion 12 can include an upper outside surface 18 and a toothpaste dispensing nozzle 20 that protrude above upper outside surface 18. Dispensing nozzle 18 can comprise an upper surface 21 and an opening 22 through the upper surface that passes internally through nozzle 20. When cap device 10 is mounted upon toothpaste container 100, a continuous pathway from container 100 through tube dispenser nozzle 102 and through cap dispenser nozzle 20 can be formed. Accordingly, toothpaste from container 100 can be dispensed through the cap device.

Bottom cap portion 12 can comprise a front surface portion 29 that in particular configurations can be angled relative to vertical sidewalls 13 of the bottom portion. A pair of raised vertical protrusions 27 can optionally be laterally spaced on either side of front surface 29 such that a seal may form between the raised protrusions and the upper cap portion when the device is in a closed position. In this embodiment a cavity may be formed between the upper and bottom cap portions (not shown) surrounding front surface 29. It is to be understood that terms such as vertical, lateral, horizontal, etc. are used herein to describe relative aspects of the invention as depicted in the figures. Accordingly, the term "vertical" refers to the depictions and the relevant feature can become "non-vertical" if the actual device is tilted.

A floss-loading slit 24 can pass through the bottom cap sidewall, preferably within the front surface portion 29 as depicted in FIG. 1. Slit 24 can be a vertical slit extending vertically from a bottom edge of the bottom cap portion. A horizontal loading slit 26 can connect to vertical slit 24 and can culminate in an opening 28 for dispensing threaded floss. Dental floss 34 can be threaded from the inside of bottom cap portion 12 (see FIG. 2), to the outside of bottom portion 12 through opening 28 by passing the floss initially through slits 24 and 26. The widths of slits 24 and 26 and the diameter of opening 28 are not limited to any particular values. Preferably these values will exceed the diameter of the dental floss being utilized to allow ease of loading through the slits and dispensing through the opening.

A floss cutter 30 can be mounted through front surface 29. Cutter 30 can comprise a raised blade 32 for cutting floss passed behind the blade. Accordingly, floss 34 can be passed from opening 28 behind blade 32 of cutter 30 and can be cut by the blade by applying pressure to the floss against the blade. Floss cutter 30 can comprise, for example, a metallic material that is bendable to allow blade 32 to be raised relative to the remaining surface of floss cutter 30.

Spacing between slit 24 and cutter 30 (center-to-center) is not limited to a particular value. The center-to-center distance can be, for example, greater than or equal to about 1.6 cm.

Still referring to FIG. 1, upper cap portion 14 is depicted in a position that illustrates an inside sidewall surface 36. Upper portion 14 has a lower edge 38 configured to contact upper surface 18 of the bottom portion 12 in a closed position (FIG. 3) forming a seal between the upper portion 14 and the bottom portion 12. A protruding ring 42 can extend from an inner top surface 40 of the upper portion. Ring 42 can be configured surround an upper portion of dispensing nozzle 20 to form a seal therebetween. Alternatively, ring 42 can be configured to contact upper surface 21 of dispensing nozzle 20 of the bottom portion in a closed position and can form a seal with the nozzle to protect the toothpaste within the nozzle when the device is not in use.

Upper cap portion 14 can comprise a tab 43 that extends below bottom edge 38 of the upper cap portion. Tab 43 can have a width that is at least as wide as a width across the pair of raised protrusions 27 (outside edge to outside edge of the raised protrusions) of bottom cap portion 12. Thus closing of cap device 10 can form a seal between tab 43 of upper cap portion 14 and bottom cap portion 12 to provide a sealed cavity across surface 29 of the bottom portion (see FIG. 3B). The sealed cavity provides protection from contaminants of otherwise exposed floss 34. Tab 43 also covers blade 32 to protect against unintentional contact and potential injury that could occur if the blade were exposed during storage. Tab 43 can also be utilized to open the upper cap portion of device 10.

Figure 2:
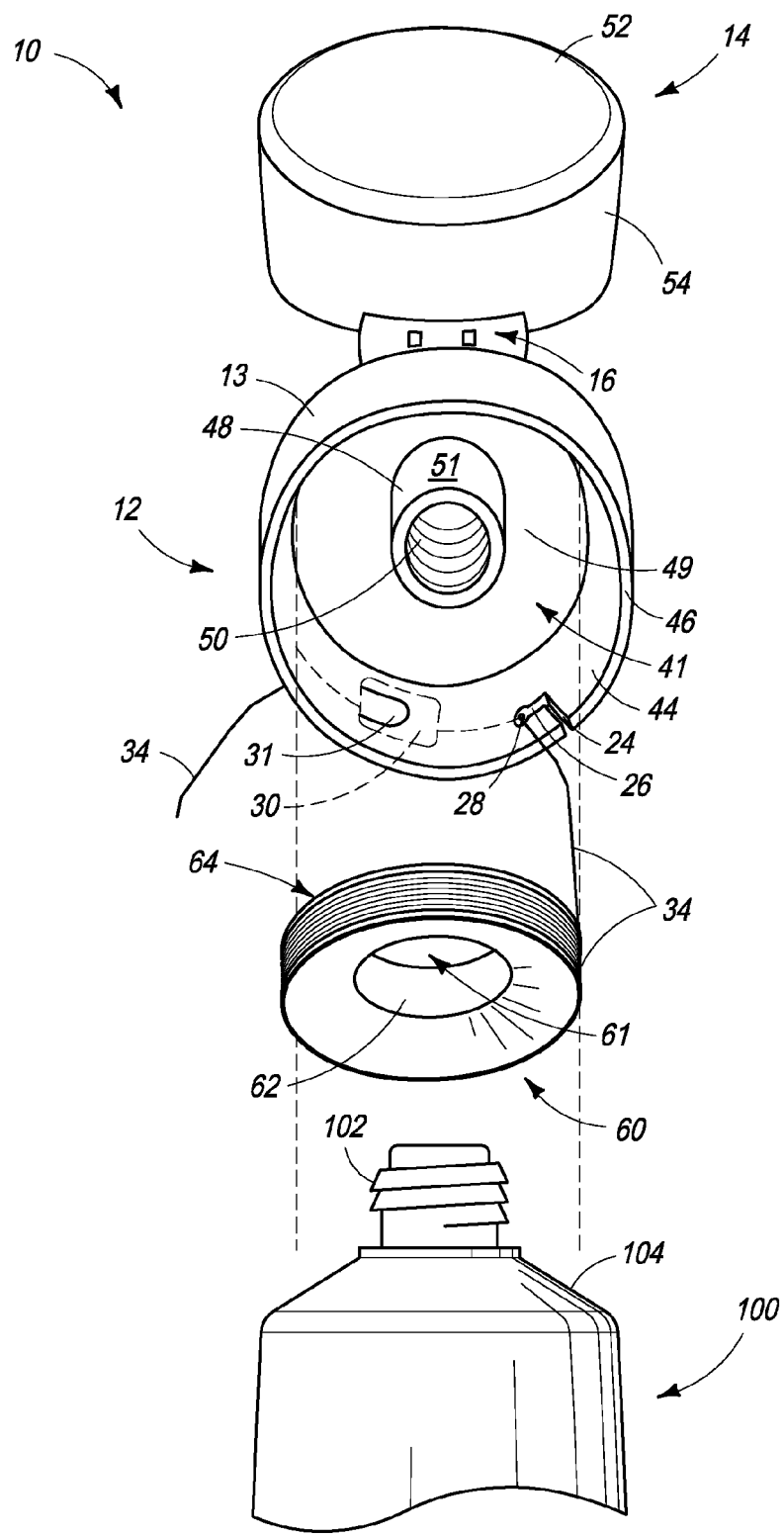
FIG. 2 shows an alternate exploded view of the embodiment of the invention illustrated in FIG. 1.

Referring next to FIG. 2, device 10 is depicted in an alternate view relative to FIG. 1. The view in FIG. 2 shows bottom cap portion 12 from below. Bottom cap portion 12 has an internal space or cavity 41 having inner sidewall surfaces 44. Bottom portion 12 additionally comprises a lower surface 46 configured to contact an upper surface 104 of toothpaste container 100 when device 10 is mounted on the container.

Bottom cap portion 12 can include a connector 48 that protrudes below an inside upper surface 49 of the bottom cap portion. Connector 48 is shown to comprise internal threads 50 which can be utilized to reversibly attach device 10 to dispensing nozzle 102 on the depicted toothpaste container 100 by threading internal threads 50 onto external threads of nozzle 102. Threads 50 can be configured to attach device 10 onto a standard toothpaste tube having a standard thread pattern as depicted. It is to be understood that alternative connection features are contemplated for utilization of device 10 with other container types.

As illustrated, floss cutter 30 can have a mounting tab 31 which can be inserted through the sidewall of bottom portion 12. Tab 31 can be bent such that the tab lies against inner sidewall surface 44 and holds the cutter in place.

As shown in FIG. 2, floss cutter 30, slits 24 and 26 and opening 28 can preferably be disposed directly opposing the position of hinge region 16 on device 10. Upper cap portion can be seen to comprise an outer sidewall surface 54 and an outer upper surface 52.

FIG. 2 also illustrates a floss spool 60 that can be configured for removable insertion and retention within cavity 41 of the bottom cap portion 12. Spool 60 can be cylindrical as depicted and can have an interior surface 62 surrounding an internal opening 61. Spool 60 can be positioned within bottom portion cavity 41 by sliding the internal opening 61 of the spool over an outer surface 51 of connecter 48. An upper surface 64 can be contacting or proximate inner upper surface 49 of bottom cap portion 12. Attachment of device 10 onto toothpaste container 100 can form an enclosed space to retain floss spool 60 within an enclosure within cavity 41 (see FIG. 4).

Figure 3A:
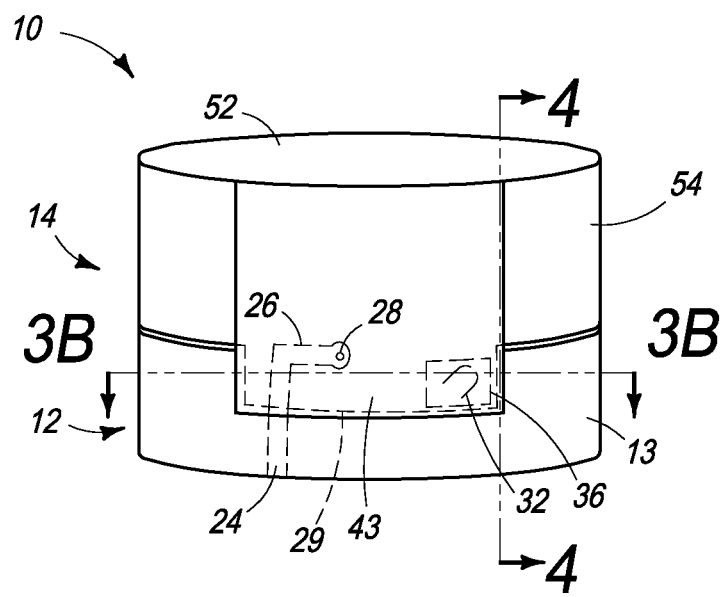
FIG. 3A illustrates an alternate view of the embodiment of the invention illustrated in FIG. 1.

Referring to FIG. 3A, such illustrates device 10 in a closed position such that tab 43 covers front surface 29 of bottom cap portion 12. In this closed position, floss leader can be covered by tab 43 and can be protected from contaminants while the device is not in use. Such configuration advantageously provides a hygienic floss dispenser with the convenience of being integral within the cap device.

Figure 3B:
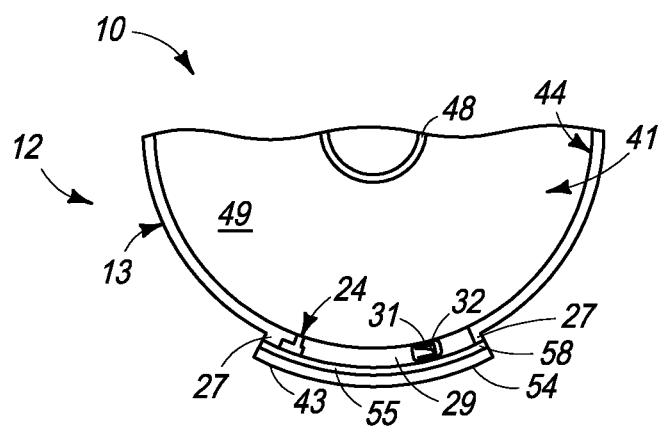
FIG. 3B is a cross sectional view of the device depicted in FIG. 3A taken along line 3B-3B of FIG. 3A

A cross sectional view of device 10 in the closed position taken along line 3B-3B is presented in FIG. 3B. This figure shows a protective cavity 55 that is formed between surface 29 of bottom portion 12 and tab 43 of upper cap portion 14. Sides of the cavity are sealed by contact of the pair of raised vertical protrusions 27 on the bottom portion with tab 43 of the upper portion 14. Leader floss (not illustrated) can be contained within protective cavity 55 externally of bottom portion 12 and internally relative to upper portion 14.

Figure 4:
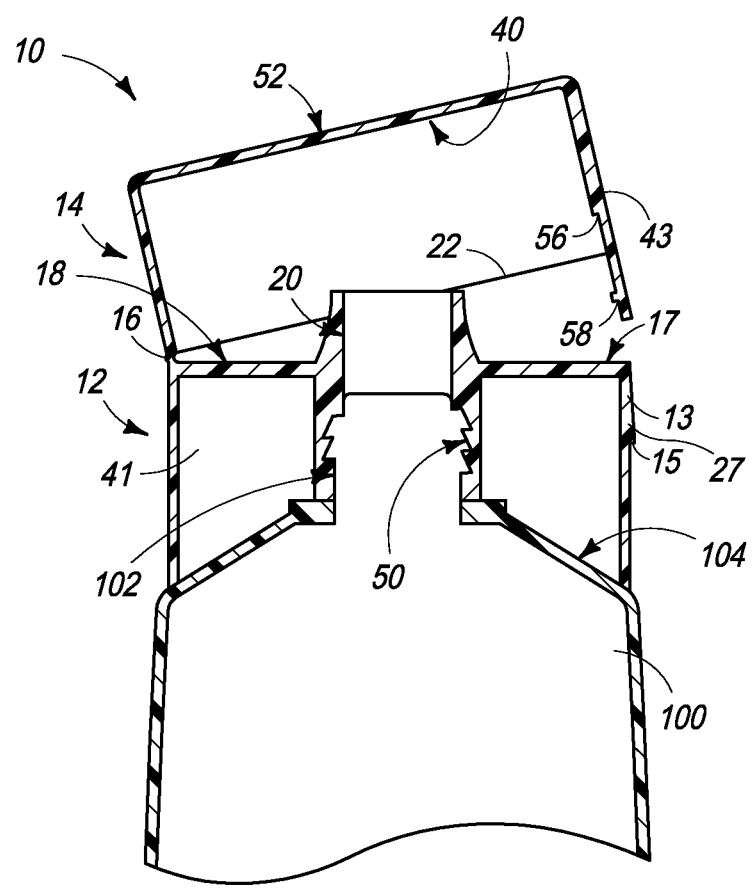
FIG. 4 shows a cross-sectional view of the embodiment of the invention shown in FIG. 3A taken along line 4-4 of FIG. 3A and further including an attached toothpaste container.

Referring to FIG. 4, such depicts a cross sectional view of device 10 taken along line 4-4 of FIG. 3A which further include cross sectional illustration of attached toothpaste container 100. As illustrated, tab 43 of upper cap portion 14 can comprises a lip 56 configured to contact an outermost region 17 of upper surface 18 comprised by bottom portion 12. Tab 43 can also have one or more protruding bar or segments 58 that can extend at least partially across an inside surface of tab 43 and can interlock with a corresponding notch 15 formed on or under raised protrusions 27 of the bottom cap portion 12. FIG. 4 also shows threads 50 of the connector portion of device 10 interlaced with the threads of dispenser nozzle 102 of the toothpaste container. It is noted that the sidewalls 13 of the bottom cap portion 12 contacts an upper surface 104 of container 100 to form an enclosure (cavity 41) for containment of a reversibly installed floss spool (not shown).

Figure 5:
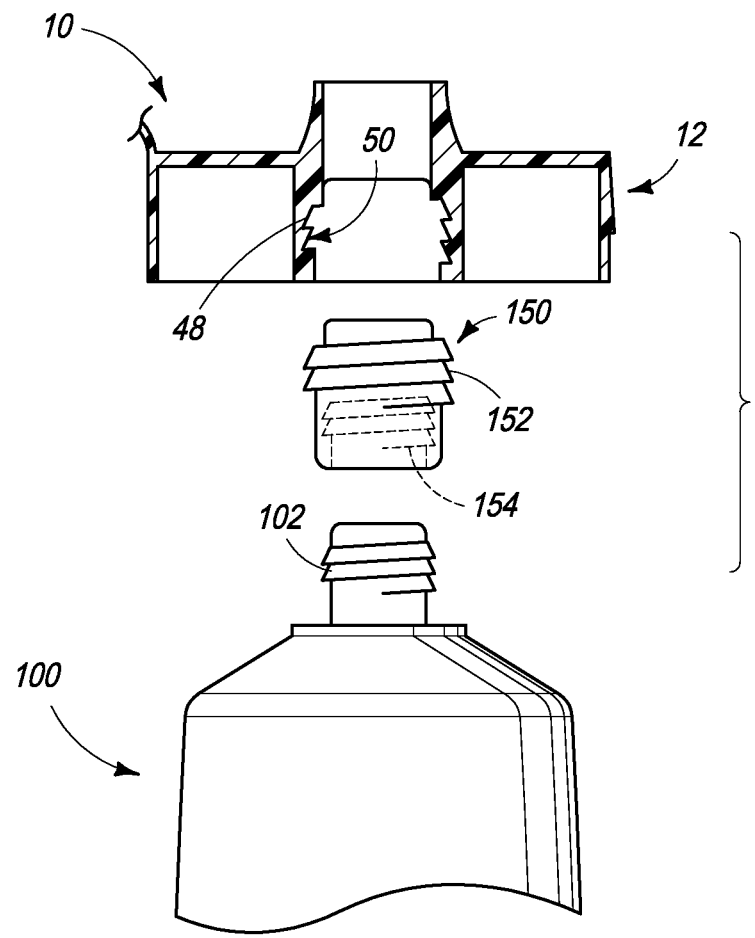
FIG. 5 illustrates an optional adaptor that can be utilized in conjunction with the invention depicted in FIGS. 1-4.

Referring to FIG. 5, an optional adaptor sleeve 150 can be provided where a non-standard toothpaste tube thread size is utilized in conjunction with device 10. Adaptor sleeve 150 can comprise internal threads 154 that match the thread pattern of the toothpaste tube. External threads 152 can be provided to thread into connector 48 of the bottom cap portion 12. In one embodiment, connector 48 can have internal threads that fit a largest size of toothpaste tube nozzle and threaded sleeves 150 of differing internal thread sizes 154 can be provided to adapt to smaller tube thread sizes such that the device can be utilized with any threaded toothpaste container. Adaptor 150 can be fabricated of a moldable plastic material that can be the same as or can differ from the material comprised by device 10. Alternatively, internal threads 50 of connector 48 can be provided to match the thread pattern of a non-standard toothpaste tube (not shown).

Figure 6:
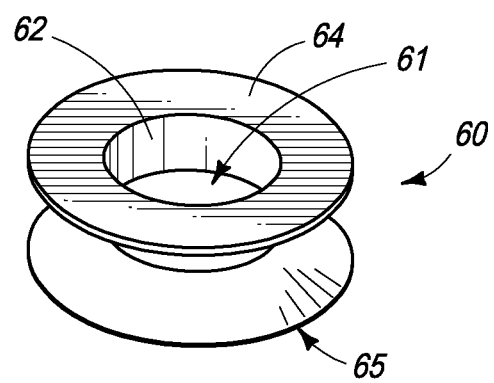
FIG. 6 illustrates a floss spool portion that can be utilized in conjunction with the embodiments of the invention depicted in FIGS. 1-5.

FIG. 6 depicts an example floss spool 60 that can be utilized in conjunction with cap device 10. Spool 60 can have a planar upper plate 64 that can be spaced from an angled lower plate 65 by a cylinder portion 62. Cylinder 62 is configured to have an opening 61 which can be slid over and reversibly mounted on connector 48. It may be preferable that both an outer surface of the connecter and inner surface 62 of the cylinder be smooth to allow easy rotation of spool 60 and dispensing of floss from the spool. Bottom plate 65 can be planar (not shown) or can be angled downward relative to the cylinder to match an angle on an upper surface of a toothpaste tube. Such angled bottom plate can additionally allow a greater amount of floss to be loaded onto the spool (up to about 40 yards).

The disclosed configuration of device 10 can allow simultaneous threading of floss through the loading slits and loading of the floss spool into the internal cavity of the bottom portion. Alternatively, floss can be threaded prior to loading of the spool. Once the spool has been loaded, dispensing device 10 can be mounted to a toothpaste tube by threading of the device onto the tube. The mounted device can contain the floss spool within the device with the tube forming a base of the enclosure as depicted in FIG. 4. The floss is thereby hygienically protected from contamination.

Device 10 can be provided in conjunction with a toothpaste container and/or can be provided independently of any toothpaste container. The floss spool can be provided together with the dispensing device and/or can be provided separately. In can be advantageous to provide an initial spool of floss together with the dispensing cap device and to additionally provide filled floss spools independently to allow refilling of the device after the initial (or subsequent) spools are depleted.

In compliance with the statute, the invention has been described in language more or less specific as to structural and methodical features. It is to be understood, however, that the invention is not limited to the specific features shown and described, since the means herein disclosed comprise preferred forms of putting the invention into effect. The invention is, therefore, claimed in any of its forms or modifications within the proper scope of the appended claims appropriately interpreted in accordance with the doctrine of equivalents.

The invention claimed is:

1. A floss dispensing toothpaste cap comprising:
   a bottom cap portion comprising a cover over an internal enclosure configured to be seated over a toothpaste tube, the bottom cap portion having an open bottom for receiving the toothpaste tube into the enclosure;
   an internally threaded connector extending downward from the cover within the enclosure, the connector having threads for connecting the toothpaste cap onto an outwardly threaded nozzle of the toothpaste tube;
   a toothpaste dispensing nozzle disposed on an outside upper surface of the cover of the bottom cap portion, the dispensing nozzle extending upward from the cover and opposing the internally threaded connector;
   a floss cutter positioned on a side of the bottom cap portion, the floss cutter having a blade external to the side of the bottom cap portion;
   a removable floss spool within the enclosure seated over the internally threaded connector, the floss spool being configured to be retained within the enclosure between an inner surface of the cover and the toothpaste tube; and
   a top cap portion connected to the bottom cap portion by a hinge region, the top cap portion comprising a tab which extends over a side of the bottom cap portion and covers the floss cutter in a closed position.

2. The cap of claim 1 wherein the bottom cap portion comprises a slot extending from a bottom edge to an opening through the side of the bottom cap portion, and wherein floss from the floss spool is threaded through the opening by way of the slot.

3. The cap of claim 2 wherein the tab covers the slot and the opening in the closed position.

4. The cap of claim 2 wherein the bottom cap portion comprises an angled recessed surface along the side, the slot, the opening and the floss cutter being positioned along the angled recessed surface.

5. The cap of claim 1 wherein the top cap portion has an inner seal protruding from an inner upper surface, the inner seal forming a seal between the inner seal and the dispensing nozzle in the closed position.

6. The cap of claim 1 further comprising an adaptor sleeve configured to adapt the internally threaded connector to the outwardly threaded nozzle of a toothpaste tube.

7. The cap of claim 1 wherein the removable floss spool comprises an angled bottom plate.

8. The cap of claim 1 wherein the tab comprises an protrusion on an inside tab surface, the protrusion being configured to fit over a ridge on an outside surface of the bottom cap portion.

\* \* \* \* \*

UNITED STATES PATENT AND TRADEMARK OFFICE
CERTIFICATE OF CORRECTION

PATENT NO. : 9,301,820 B2  
APPLICATION NO. : 14/483017  
DATED : April 5, 2016  
INVENTOR(S) : John Karl Hintz Page 1 of 1

It is certified that error appears in the above-identified patent and that said Letters Patent is hereby corrected as shown below:

IN THE SPECIFICATION

Column 1, line 23 – Replace "cap devises" with --cap devices--

Column 3, line 27 – Replace "surround an" with --to surround an--

Column 4, line 38 – Replace "comprises a lip" with --comprise a lip--

Column 5, lines 25-26 – Replace ". In can be" with --. It can be--

Signed and Sealed this  
Seventh Day of June, 2016

Michelle K. Lee  
*Director of the United States Patent and Trademark Office*